United States Patent [19]

Storz

[11] 4,294,235
[45] Oct. 13, 1981

[54] LARYNGOSCOPE

[76] Inventor: Karl Storz, Auf dem Schildrain 39, 7200 Tuttlingen, Fed. Rep. of Germany

[21] Appl. No.: 959,703

[22] Filed: Nov. 13, 1978

[30] Foreign Application Priority Data
Nov. 26, 1977 [DE] Fed. Rep. of Germany ... 2751990

[51] Int. Cl.$^3$ .......................... A61B 1/06; A61B 1/26
[52] U.S. Cl. .................................................. 128/11
[58] Field of Search .................................. 128/3–11, 128/15, 16–19, 22, 23, 173.3, 303.15, 199, 201, 208, 351, 200.15, 203.18

[56] References Cited

U.S. PATENT DOCUMENTS

| | | | |
|---|---|---|---|
| 2,070,820 | 2/1937 | Allyn | 128/11 |
| 2,648,329 | 8/1953 | Mörch | 128/11 |
| 3,384,076 | 5/1968 | Speelman | 128/9 |
| 3,481,325 | 12/1969 | Glassman | 128/8 |
| 3,677,262 | 7/1972 | Zukowski | 128/6 |
| 3,934,578 | 1/1976 | Heine | 128/9 |
| 3,976,054 | 8/1976 | Evans | 128/4 |
| 4,106,493 | 8/1978 | Proctor et al. | 128/9 |
| 4,126,127 | 11/1978 | May | 128/11 |

FOREIGN PATENT DOCUMENTS

| | | | |
|---|---|---|---|
| 530194 | 9/1956 | Canada | 128/11 |
| 7011282 | of 0000 | Fed. Rep. of Germany | |
| 610466 | 6/1926 | France | 128/4 |
| 7126 | of 1903 | United Kingdom | 128/4 |

*Primary Examiner*—Robert W. Michell
*Assistant Examiner*—Arthur S. Rose
*Attorney, Agent, or Firm*—Donald D. Mon

[57] ABSTRACT

An injection breathing laryngoscope which includes an outer laryngoscope tube having a proximal and a distal open end, said tube having an inner wall which forms a passage between the ends, and an insert tube insertable into the proximal end of said passage, and itself having an inner and an outer wall, the inner wall defining a second passage open from end to end. The outer wall of the insert fits in the inner wall of the laryngoscope tube, and the inner wall of the insert supports a fiber optics bundle tube and a gas injection tube, the insert, when fully installed in the laryngoscope tube, terminates within the laryngoscope tube at a location substantially spaced from the distal end of the laryngoscope tube. The tubes are rotatable relative to one another. If desired, the inner wall of the laryngoscope tube and the outer wall of the insert tube can have matching, locking conical tapers to lock the tubes in an adjusted relative position.

3 Claims, 2 Drawing Figures

LARYNGOSCOPE

BACKGROUND OF THE INVENTION

In general a direct laryngoscopy is carried out under complete narcosis. Two different methods are used for breathing purposes, injection breathing and intubation. In the case of intubation, the breathing gas is introduced into the trachea via a tube. However, this has the disadvantage that the tube is located between the vocal chords and often impedes observation. Therefore, generally preference is nowadays given to injection breathing for which an injection nozzle is positioned within the internal diameter of the laryngoscope rim and is used for blowing in the breathing gas under pressure. The invention relates to such a laryngoscope.

However, the prior art constructions have the disadvantage that the injection nozzle cannot always be positioned in an optimum manner with adequate ease. Thus, if for example there is a swelling on the vocal chords in the direction in which the breathing gas is blown, it is no longer possible for the patient to breathe because the swelling swells even further due to the impinging gas flow. Therefore, suspension devices are known which enable the nozzle to be brought into various positions. However, not only is this complicated, but also the field of view can be impeded by the suspended devices.

In the case of simple, short examinations, it is conventional practice to provide the laryngoscope handle with a hook permitting the person carrying out the observation to manually control the instrument and hold it by exerting pressure. In the case of longer examinations and operations when the doctor requires both hands, the handle grip is replaced by a supporting device having a supporting rod which is longitudinally displaceable and whose angular position relative to the handle is adjustable. At the lower end of said supporting rod, there is a breast or chest support constructed as a ring (German Utility Model No. 7,011,282). This increases the pressure surface of the chest support, which also substantially adapts to the unevennesses of the chest.

BRIEF SUMMARY OF THE INVENTION

The problem of the invention is to so improve the laryngoscope of the type indicated hereinbefore that the disadvantages resulting from the gas stream cannot occur. In particular, it must be possible to easily and advantageously move the nozzle into all the different rotational positions, without the field of vision being disturbed by a corresponding device.

According to the invention, this problem is solved in that the injection nozzle is arranged in an insert separable from the laryngoscope tube and that the insert is rotatable about its longitudinal axis and can be secured in various positions.

As a result of the separate insert, the rotation position of the nozzle can be modified very easily without a separate device, so that the field of vision is not impeded.

According to a further development of the invention, a fibre glass light guide is arranged in the insert. This simultaneously ensures an adequate illumination of the viewing or operating field without requiring additional devices which could unnecessarily constrict the cross-section.

According to a further feature of the invention, the insert has a conical outer surface corresponding to a matching conical inner surface of the laryngoscope tube.

This conical construction has the important advantage that it can be easily secured in any random position if the cone is made sufficiently large to have a self-locking action. It is also possible to lock the insert in any random position by gently pressing in. In addition, only limited force is required to detach it by drawing out. It is advantageous for the insert to be much shorter in its longitudinal direction that the laryngoscope tube.

Thus, the mouth of the nozzle is not arranged at the proximal end of the laryngoscope tube in the known manner and instead is positioned in the centre thereof. Thus, to a certain extent the gas steam diverges, so that it does not have, or at least does not have to the same extent, the above-mentioned prejudicial action when striking the inside of the cavity of the patient. In certain cases, this measure alone is sufficient to solve the above-indicated problem.

BRIEF DESCRIPTION OF THE DRAWINGS

Further advantages and details of the invention can be gathered from the following description of a non-limitative embodiment, with reference to the drawings wherein.

DETAILED DESCRIPTION OF THE PREFERRED EMBODIMENTS

Figures 1, 2:
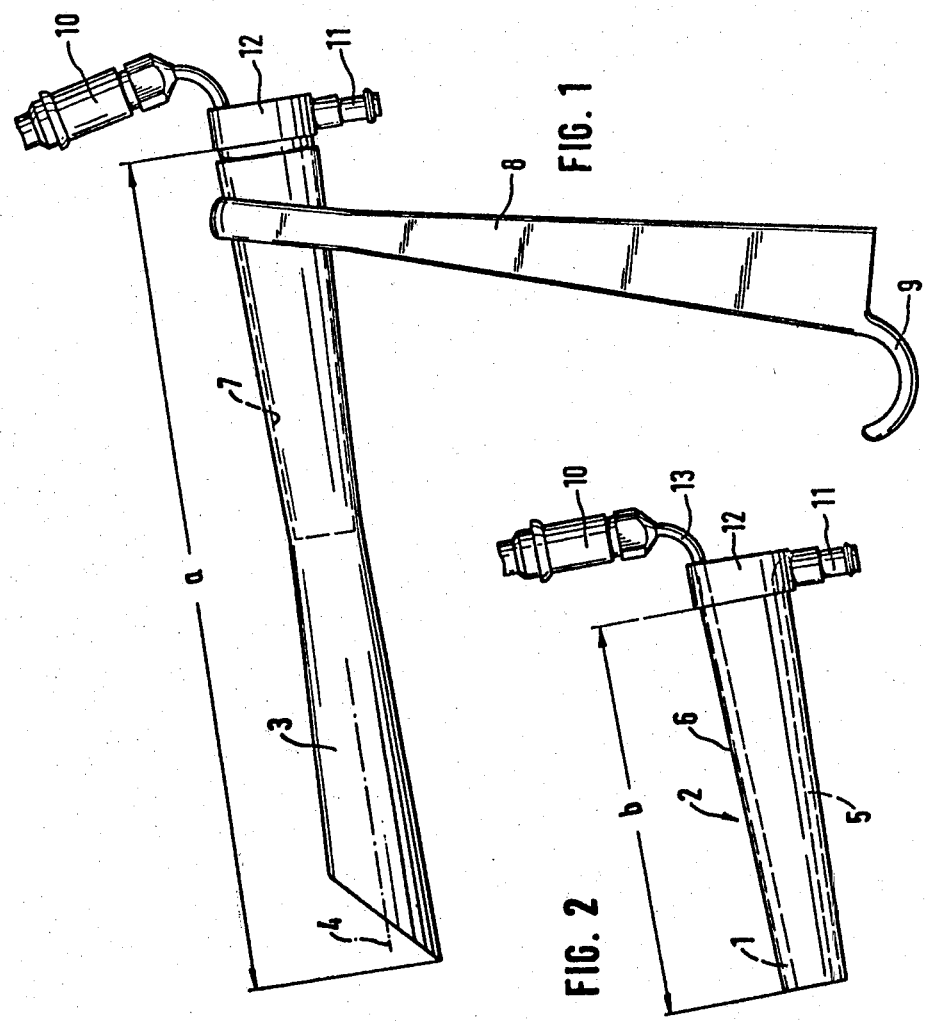
FIG. 1 is a side view of the complete laryngoscope in the fitted state.
FIG. 2 is a side view of the insert according to the invention.

FIG. 1 shows the closed laryngoscope tube 3 with a connection 11 for the injection gas and a further connection 10 for the fibre glass light guide at the proximal end.

The total length of laryngoscope tube 3 is designated by a. The head piece 12 at the proximal end forms part of the separate insert tube according to the invention (FIG. 2), which is inserted into the tube 3 of FIG. 1 in the direction of rotation axis 4. In addition, a handle 8 with a hook 9 is arranged in conventional manner on laryngoscope 3, whilst in addition the above-mentioned known holding device can be used.

FIG. 2 shows the removed insert 2, whose head piece 12 only is visible in FIG. 1. It is externally provided with a conical surface 6, which is matched by a corresponding inner cone 7 inside the laryngoscope tube 3. Advantageously, the taper of cone 6 is made so small that self-locking occurs with only gentle insertion into tube 3.

The total length of this cone within tube 3 is designated as b, which is only approximately half as large as a of laryngoscope tube 3.

FIG. 2 also shows by means of broken lines the extension of injection tube 5 up to the injection nozzle, said tube 5 being welded to the inner surface of the insert so that it takes up the minimum cross-sectional area. In the same way, the fibre glass light guide 13 is e.g. guided along the opposite inner surface of insert 2 up to the distal end 1 thereof.

Hereinafter, the operation of the invention is described. The insert according to FIG. 2 is slightly inserted into the laryngoscope tube in the direction of axis 4 in FIG. 1. If cone 6, 7 is constructed with a self-locking angle, then a very limited pressure is necessary for locking purposes. It is then firmly seated in tube 3 and can only be detached by being removed rearwards in the proximal direction in the direction of the axis.

The invention is not restricted to the represented embodiment and for example an annular light guide can be provided in the centre of the tube and an extension of light guide 13 up to the distal end, so that even with said rotation the light guide is maintained.

What is claimed is:

1. An injection breathing laryngoscope comprising: a laryngoscope tube having a proximal and a distal end, an axis, and an inner wall defining an axial passage from end to end, an insert tube having a proximal and a distal end, an axis, an inner wall defining an axial passage from end to end, and an outer wall so proportioned and arranged as rotatably to fit in said inner wall of said laryngoscope tube entering the proximal end of said laryngoscope tube, and having an axial length substantially shorter than that of the laryngoscope tube so that its distal end lies within said laryngoscope tube and substantially spaced from the distal end of said laryngoscope tube; fiber optics means and a breathing gas tube inside the insert tube passage and attached to said insert tube and terminating at said distal end of said insert tube, said inner wall of said laryngoscope tube and said outer wall of said insert tube having matching conical axially extending locking tapers, whereby said tubes can be rotated relative to one another with said tubes axially spaced apart, and locked in an adjusted position by pressing them axially together, and in which said laryngoscope tube flares outwardly from a medial location to its distal end.

2. An injection breathing laryngoscope according to claim 1 in which said fiber optics means and said breathing gas tube are attached to said inner wall of said insert tube.

3. An injection breathing laryngoscope according to claim 1 in which said breathing gas tube is welded to said insert tube.

* * * * *